United States Patent [19]

Hooper et al.

[11] 4,439,421

[45] Mar. 27, 1984

[54] STABILIZED GAMMA GLOBULIN CONCENTRATE

[75] Inventors: John A. Hooper, Santa Ana; Samia Mankarious, Costa Mesa; Catherine R. Liu-Rash, Mission Viejo, all of Calif.

[73] Assignee: Baxter Travenol Laboratories, Inc., Deerfield, Ill.

[21] Appl. No.: 413,060

[22] Filed: Aug. 30, 1982

[51] Int. Cl.$^3$ ..................... A61K 39/00; A61K 35/14
[52] U.S. Cl. ........................................ 424/85; 424/101
[58] Field of Search ................................. 424/85, 101

[56] References Cited

U.S. PATENT DOCUMENTS

| | | | |
|---|---|---|---|
| 3,105,012 | 9/1963 | Brandon et al. | 167/78 |
| 3,415,804 | 12/1968 | Polson | 260/112 |
| 3,804,754 | 4/1974 | Ishil et al. | 210/23 |
| 3,966,906 | 6/1976 | Schultze et al. | 424/85 |
| 4,089,778 | 5/1978 | Gauger | 210/23 F |
| 4,093,606 | 6/1978 | Coval | 260/112 B |
| 4,124,576 | 11/1978 | Coval | 260/112 B |
| 4,126,605 | 11/1978 | Schneider et al. | 260/112 B |
| 4,165,370 | 8/1979 | Coval | 424/85 |
| 4,312,949 | 1/1982 | Ahrens | 435/272 |

FOREIGN PATENT DOCUMENTS 1469908  4/1977  United Kingdom .
1597204  9/1981  United Kingdom .

OTHER PUBLICATIONS

Schneider et al., "Diagnostik"; Estimated Publication Date 1976.
Hack et al., "Chem. Abstracts" 95:130743s (1981).
Schneider et al., "Vox Sang." 31:141-151 (1976).
Gislason et al., "Vox Sang." 34:143-148 (1978).
Lundblad et al., "Pharmaceuticals" 92:185911p (1980).
Tukachinskii et al., "Pharmaceuticals" 87:157106h (1977).
Funakoshi et al., "Chem. Abstracts" 90:174665u (1979).
Habeeb et al., "Vox Sang." 32:143-158 (1977).
Markovskii et al.-Chem. Abst. vol. 87, (1977), p. 165,886c.

Primary Examiner—Sam Rosen
Attorney, Agent, or Firm—Max D. Hensley; P. C. Flattery

[57] ABSTRACT

Gamma globulin concentrates are stabilized against anticomplement activity generation during lyophilization by inclusion in the concentrate of a physiologically acceptable, substantially nonsurface-active hydrophilic macromolecule. The improved concentrates may be safely administered to patients. The main additives to the gamma globulin are a substantially nonsurface-active hydrophilic macromolecule, a protein and a polyol.

27 Claims, No Drawings

STABILIZED GAMMA GLOBULIN CONCENTRATE

This invention relates to immunoglobulins. It is concerned particularly with gamma globulin preparations acceptable for intravenous administration and to methods for making same.

Gamma globulin, also known as immune serum globulin or IgG, is a protein fraction found in the plasma of higher animals. It contains a large number of antibodies having specificity and in comparative proportions dependent upon the plasma donor's exposure to antigens, e.g. by way of vaccinations. This fraction is clinically useful in the treatment and prophylaxis of microbial diseases. Relatively purified gamma globulin fractions have been known for over thirty years. Such fractions have a gamma globulin proportion greater than that found in normal pooled human plasma. They are termed gamma globulin concentrates for the purpose herein.

Many gamma globulin concentrates are unsafe for intravenous inJection because administration by this route can result in patient shock, particularly hypotensive circulatory failure. Attempts have been made to obviate this hazard by intramuscular injection. However, side effects such as, nausea, vomiting, pyrexia, rigora, backache and severe pain at the injection site have remained a problem. In addition, intramuscular injection considerably reduces the gamma globulin efficacy because of slow diffusion of the gamma globulin into the blood stream and local proteolysis of the protein.

The adverse side effects have been linked to activity which develops in the concentrates during their preparation and liquid storage, activity which is termed anticomplement activity. This activity in turn has been linked to the formation of gamma globulin aggregates. Such aggregates also present an undesirable turbidity in the gamma globulin concentrates.

The art has endeavored to prepare gamma globulin which exhibits low anticomplement activity and can thus be intravenously injected without the hazards and side effects encountered with early gamma globulin compositions. Attempts to reduce anticomplement activity have included pepsin or plasmin digestion of the concentrates, B-propiolactone treatment, fractionation methods which use polyethylene glycol as precipitating agent, and other techniques described in U.S. Pat. Nos. 4,093,606; 4,126,605; 3,966,906 and 4,124,576. Some methods have enlisted the aid of additive hydrocolloids, glycerol, xylitol, mannitol, sorbitol, glycine, albumin and nonionic surfactants to stabilize the gamma globulin against aggregate formation.

These methods have failed to realize the combined objectives of satisfactorily low levels of stabilizers in the final concentrate, acceptably low anticomplement activity, high product yield, manufacturing simplicity and gamma globulin integrity. The objects of this invention include meeting these combined objectives in a fashion that has not heretofore been possible. These and other objects of this invention will be apparent to those skilled in the art from a study of this specification as a whole.

SUMMARY OF THE INVENTION

The objects of this invention are achieved by including a physiologically acceptable, substantially nonsurface-active hydrophilic macromolecule with gamma globulin concentrates during lyophilization of the concentrates. Particularly desirable results are obtained when the gamma globulin concentrates are lyophilized with the hydrophilic macromolecule and, in addition, a supplemental protein and/or a physiologically acceptable low molecular weight polyol. The resulting dry compositions, containing stabilizing amounts of the macromolecule and the protein and/or polyol, exhibit low anticomplement activity without the presence of large quantities of any one stabilizer.

DETAILED DESCRIPTION OF THE INVENTION

The gamma globulin concentrates to which the stabilizers are to be added may be obtained from tissues, lymphocyte hybridoma cultures, blood plasma or serum, or recombinant cell cultures by any suitable fractionation procedure, e.g., alcohol precipitations, ion exchange separations and the like. The relative proportion of gamma globulin to total protein in the concentrate is not critical, but will be greater than that of the starting material. This means that the gamma globulin is enriched compared to the starting material. Ordinarily it is desirable to leave a small residue of nongamma globulin protein in the concentrate so that exogenous protein need not be supplied if it is decided to use a protein stabilizer during lyophilization. The typical gamma globulin concentrates will contain greater than about 80%, preferably greater than about 96% gamma globulin by weight of total protein. These concentrates should have low anticomplement activity and preferably the gamma globulin will be intact, i.e., not previously digested with proteolytic enzymes to reduce anticomplement activity. The concentrates will have a high solids level, typically a protein level of about 50 g/liter or greater, but this is more a matter of economics in reducing lyophilization time.

The concentrate may contain a high titer for a particular antigen or class of antigens of interest. This means that the concentrate will have a greater proportion of antibodies specific for such an antigen or class of antigens than is found in pooled normal plasma. Such "hyperimmune" globulin concentrates will usually contain high titers for various cellular or viral pathogens such as Clostridium or hepatitis.

The macromolecule to be included with the gamma globulin concentrate prior to lyophilization will have an average molecular weight greater than about 1000 Daltons, preferably about from 3000 to 50,000 Daltons. It usually will be a polymer, and is desirably a polymer which can be metabolized to innocuous monomers in the patient's circulation and/or readily excreted. Polymers are infrequently available in which every molecule is of the same molecular weight. Accordingly, molecular weights disclosed herein shall be considered average, with the actual molecular sizes ranging plus or minus up to about 30%.

The macromolecule preferably is nonproteinaceous. The reason for this is that synthetic proteinaceous amides or proteins from nonhuman sources are frequently antigenic upon administration to patients, and proteins from human sources are comparatively ineffective in preventing the generation of anticomplementary activity during lyophilization.

The macromolecule should be sufficiently water soluble, hence hydrophilic, to supply a gamma globulin-stabilizing concentration of macromolecule. This generally means the macromolecule is soluble in saline at room temperature at a concentration of at least 3% weight/volume. Obviously, this requirement will change depending upon the degree of dilution of the gamma globulin concentrate; lower protein concentrations require less macromolecule, and thus the solubility can be lower. Slight turbidity imparted by colloidal particles of water insoluble macromolecule at saturation concentrations of macromolecule are tolerable if the particles are not of a size to be a hazard to patients. However, it is preferred that the macromolecule be used in a concentration at which it is completely soluble in the concentrate solution.

This invention contemplates adding the macromolecule to gamma globulin concentrates as a solid or as a predissolved solution. It may be necessary to heat or otherwise treat the macromolecule to form a solution. In such a case the macromolecules should not gel, precipitate or crystallize upon cooling or removal of the dissolution treatment.

The macromolecule is part of a composition intended for infusion or injection, and accordingly it should be physiologically acceptable. This means that the macromolecule should not be toxic to patients when the concentrate is administered at dosages and over periods therapeutically effective for the gamma globulin within the concentrate. This generally requires that the macromolecule exhibit little or no surface active properties as such materials may adversely affect blood cells. Thus, the macromolecule should be free of any substantial nonionic or ionic surfactant character, i.e. be substantially nonpolar thereby excluding any of the nonionic surfactants specifically disclosed in U.S. Pat. No. 4,093,606.

Suitable macromolecules ordinarily will fall within three general classes: polyethers, polysaccharides and hydrophilic vinyl polymers. Generally the first class is preferred for maximal gamma globulin stability, with polysaccharides being most preferred for physiological acceptability.

Suitable polyethers are generally polyethers synthesized from hydroxylated monomers. They include polymers having the following general structure:

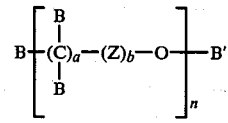

wherein B' is H, B is H, —OH, —NH$_2$, —CH$_2$OH, —CH$_2$NH$_2$, or —CH$_2$COOH, a is 1 to 3, n is greater than about 20, Z is CH$_2$, b is zero or 1; and block copolymers of such polymers. Polyethylene glycol is the preferred polymer.

The polysaccharides which may be employed include branched and unbranched polymers (n>3) of five and-/or six carbon sugars, including such sugars as ribose, xylose, mannose, glucose, galactose and fructose, and derivatives thereof. Exemplary polysaccharides are starch, glycogen, hydroxyethyl starch, polyglucose, dextran, xylan, pectin, acacia and hydrolysates thereof.

The hydrophilic vinyl polymers are polyhydroxy-substituted or carry other hydrophilic substituents. Examples include polyvinyl alcohol or polyvinylpyrrolidone. Polyethylene glycol is preferred over all other hydrophilic macromolecules.

Other physiologically acceptable, substantially non-surface-active hydrophilic macromolecules will be apparent to the ordinary artisan, and may be selected by combining the macromolecule with gamma globulin concentrates, lyophilizing and thereafter assaying in known fashion for the inhibition of anticomplementary activity generation during the lyophilization process. Mixtures of different macromolecule species may be employed.

The amount of macromolecule to be used is subject to some discretion. The optimal quantity should be determined by routine experimentation, but it will generally range in a weight ratio to the total protein present in the gamma globulin concentrate of about from 0.0075 to 0.062, preferably about from 0.01 to 0.05. This quantity must be more than trace or residual levels remaining after a precipitation step in which gamma globulin is precipitated from a solution containing the macromolecule. Thus, while the macromolecule may be present during or prior to precipitation or adsorption steps in gamma globulin purification procedures, if such procedures include a protein precipitation step in which a gamma globulin-containing protein is precipitated in and recovered from a solution containing the macromolecule, then a supplementary amount of the macromolecule should be added to the redissolved, precipitated protein before it is lyophilized.

Particularly beneficial results are obtained by using the macromolecule in concert with two other classes of gamma globulin stabilizers: Proteins and low molecular weight polyols. Substances which fall within these classes (albumin and mannitol, respectively, U.S. Pat. Nos. 4,093,606 and 4,124,576) are known as lyophilization stabilizers for gamma globulin. The use of a combination of such stabilizers along with the hydrophilic macromolecule permits the use of less of each stabilizer than would have been the case if any one stabilizer had been employed alone.

Stabilizing protein may be supplied as residual protein remaining after purification of the gamma globulin, as discussed above. Alternatively and preferably a supplemental amount of protein is added to the solution of gamma globulin concentrate to be lyophilized. This supplemental amount is added so that the ratio of exogenous protein to total protein in the concentrate is about from 0.01 to 0.125, preferably 0.01 to 0.05, by weight. Albumin is the preferred protein, although other water soluble, physiologically acceptable, substantially nonantigenic proteins are satisfactory.

The polyol is a compound having a molecular weight of less than about 1000 Daltons and a high degree of substitution by hydroxyl groups, generally up to about seven hydroxyl groups per molecule. The polyol is to be physiologically acceptable in the concentrations contemplated herein, so the preferred polyols di and trisaccharides, sugar alcohols or reducing and nonreducing monosaccharides. Exemplary polyols include mannitol, sorbitol, glucose, mannose, lactose, fructose and maltose. Glucose is most preferred.

The amount of polyol to be used shall be determined in the same fashion as described above for the macromolecule and protein, although typical amounts range in a weight ratio to total protein in the concentrate of from about 0.05 to 1.25, preferably 0.1 to 0.5. A stabilizing quantity of an amino acid such as glycine also may be included with the macromolecule, protein and polyol.

The starting gamma globulin concentrates are typically dissolved in a solution containing the hydrophilic macromolecule along with whatever other stabilizers are selected, although it is within the scope of this invention to add the stabilizers in their dry state to concentrate solutions. The protein level in such solutions is typically adjusted to about 50 to 100 mg/ml, of which about 80% or more by weight is gamma globulin. The solutions will contain sodium chloride or other isotonicity agent and have a pH around neutrality. Once all additions to the solution have been made, it is passed through a filter capable of retaining cellular microorganisms and sterile filled into vials or other suitable containers. The concentrate is then freeze-dried by conventional procedures and the containers hermetically sealed.

The lyophilized concentrate is reconstituted in sterile water to a protein concentration of 5.2% and injected intravenously into patients.

EXAMPLE 1

A solution of gamma globulin concentrate containing intact gamma globulin at 98% by weight of total protein, a total protein concentration of 52 g/L, 1.0 g/L heat treated human albumin, 20 g/L glucose, 22.5 g/L glycine, 1.0 mg/ml polyethylene glycol 4000 and 8.5 g/L NaCl at pH 7.0 was passed through a 0.2 u filter and filled into 50 ml vials. The contents of the vials were lyophilized and the vials then sealed. The vial contents were reconstituted into the same volume of water and assayed for anticomplementary activity using the following method:

Anticomplement activities were determined by diluting immunoglobulin samples with albumin veronal buffer (veronal buffered saline, pH 7.4, containing 20 mg/ml normal serum albumin, hereafter AVB) and assaying each sample dilution for complement activity. In this assay, 1.0 ml of each dilution was incubated with 1.0 ml of guinea pig complement (2 CH50 units) and 4.5 ml of AVB at 37°. Control tubes containing 2 CH50 units of complement in 6.5 ml of AVB were also incubated at 37°. At the end of the 60 minute incubation period, all samples were transferred to an ice water bath and $5 \times 10^8$ hemolysin-sensitized erythrocytes in 1.0 ml of AVB were added to each tube. The suspensions were incubated for 90 minutes at 37°, were cooled in an ice water bath and were centrifuged at 5°. The absorbance of the supernatants was measured at 541 nm. The percentage hemolysis in each test sample was calculated using the absorbance of the complement control samples (2 CH50 units) as 100% hemolysis. The complement activity of each dilution of the test sample is plotted against percent hemolysis to obtain the amount of test sample which binds 1.0 CH50 unit of guinea pig complement. Anticomplement activities obtained by this procedure are reported as CH50 units per gram of protein in the immunoglobulin sample.

The anticomplement activity was less than 200 CH50 units/gram, and in many vials was less than 150 CH50 units/gram.

We claim:

1. A stabilized gamma globulin concentrate comprising gamma globulin (a) a water soluble, physiologically acceptable, substantially nonsurface-active hydrophilic macromolecule having a molecular weight greater than about 1000 Daltons, (b) a water soluble, physiologically acceptable protein other than gamma globulin and (c) a water soluble, physiologically acceptable polyol having a molecular weight less than the average molecular weight of the hydrophilic macromolecule, said macromolecule, protein and polyol being present, respectively, in a weight ratio to total protein in the concentrate of (a) about from 0.0075:1 to 0.062:1, (b) about from 0.01:1 to 0.125:1 and (c) about from 0.05:1 to 1.25:1.

2. The concentrate of claim 1 which is dry.

3. The concentrate of claim 1 which additionally comprises a gamma globulin stabilizing amount of the amino acid glycine.

4. The concentrate of claim 1 wherein the macromolecule has an average molecular weight greater than about 1000 Daltons.

5. The concentrate of claim 1 wherein the macromolecule is a polyether or polyhydroxy compound.

6. The concentrate of claim 5 wherein the macromolecule is a hydrophilic vinyl polymer.

7. The concentrate of claim 5 wherein the macromolecule is a polysaccharide.

8. The concentrate of claim 7 wherein the macromolecule is polyglucose.

9. The concentrate of claim 5 wherein the macromolecule is polyethylene glycol.

10. The concentrate of claim 9 wherein the polyethylene glycol has an average molecular weight of about 4000 Daltons.

11. The concentrate of claim 1 wherein the macromolecule is substantially nonpolar.

12. The concentrate of claim 1 wherein the macromolecule is present in a ratio to total protein of about from 0.01 to 0.05 by weight.

13. The concentrate of claim 1 wherein the protein is human serum albumin.

14. The concentrate of claim 1 wherein the protein is present in a ratio to total protein of about from 0.01 to 0.05 by weight.

15. The concentrate of claim 1 wherein the polyol has a molecular weight below about 1000 Daltons.

16. The concentrate of claim 1 wherein the polyol contains less than about seven hydroxyl groups.

17. The concentrate of claim 1 wherein the polyol is a sugar, sugar alcohol or oligomer thereof containing less than four monomers.

18. The concentrate of claim 17 wherein the polyol is a nonreducing sugar.

19. The concentrate of claim 17 wherein the polyol is glucose.

20. The concentrate of claim 1 wherein the polyol is present in a ratio to total protein of about from 0.1 to 0.5 by weight.

21. The concentrate of claim 20 wherein the ratio is about 0.5.

22. The concentrate of claim 1 wherein the concentrate is in aqueous solution at a concentration of about from 40 to 100 mg gamma globulin/ml.

23. The concentrate of claim 1 in a hermetically sealed container.

24. The concentrate of claim 1 which is sterile.

25. The concentrate of claim 1 which is substantially free of nonionic surfactant.

26. The concentrate of claim 1 which is free of the block copolymer of polypropylene glycol and polyethylene glycol.

27. A stabilized gamma globulin concentrate comprising gamma globulin (a) polyethylene glycol of a molecular weight greater then about 1000 daltons, (b) a water soluble, physiologically acceptable protein other than gamma globulin and (c) a water soluble, physiologically acceptable polyol selected from the group of sugars, sugar alcohols or oligomers thereof, the polyethylene glycol, protein and polyol being present, respectively, in a weight ratio to total protein in the concentrate of (a) about from 0.0075:1 to 0.062:1, (b) about from 0.01:1 to 0.125:1 and (c) about from 0.05:1 to 1.25:1.

* * * * *